(12) United States Patent
Morelli et al.

(10) Patent No.: US 12,721,651 B2
(45) Date of Patent: Sep. 1, 2026

(54) EXPANDABLE INTRODUCER

(71) Applicant: Medtronic, Inc., Minneapolis, MN (US)

(72) Inventors: Fionnuala Morelli, Belfast (GB); Emma Harvey, Armagh (GB)

(73) Assignee: Medtronic, Inc., Minneapolis, MN (US)

( * ) Notice: Subject to any disclaimer, the term of this patent is extended or adjusted under 35 U.S.C. 154(b) by 4 days.

(21) Appl. No.: 18/624,078

(22) Filed: Apr. 1, 2024

(65) Prior Publication Data

US 2024/0358403 A1 Oct. 31, 2024

Related U.S. Application Data

(60) Provisional application No. 63/498,841, filed on Apr. 28, 2023.

(51) Int. Cl.

*A61B 17/34* (2006.01)
*A61M 25/00* (2006.01)
*A61M 25/06* (2006.01)

(52) U.S. Cl.

CPC .. *A61B 17/3439* (2013.01); *A61B 2017/3433* (2013.01); *A61M 2025/0025* (2013.01); *A61M 2025/006* (2013.01); *A61M 25/0662* (2013.01)

(58) Field of Classification Search

CPC ............ A61B 17/3431; A61B 17/3439; A61B 2017/3433; A61B 2017/3443;

(Continued)

(56) References Cited

U.S. PATENT DOCUMENTS

2005/0245892 A1* 11/2005 Elkins ............... A61M 25/0043 604/264
2007/0051375 A1* 3/2007 Milliman ........... A61B 17/0218 128/856

(Continued)

FOREIGN PATENT DOCUMENTS

WO 1984001512 A1 4/1984
WO 1998029026 A2 7/1998
WO 2022026026 A1 2/2022

OTHER PUBLICATIONS

Extended European Search Report, EP Application No. 24171561.4, mailed Oct. 8, 2024, 9 pages.

(Continued)

*Primary Examiner* — Robert A Lynch
(74) *Attorney, Agent, or Firm* — Medler Ferro Woodhouse & Mills PLLC

(57) ABSTRACT

An expandable introducer includes an introducer hub and an introducer sheath coupled to the introducer hub and extending distally therefrom. The introducer sheath includes a sheath wall, the sheath wall having an interior surface defining a lumen of the introducer sheath and an exterior surface disposed radially outward from the interior surface. The exterior surface may be wavy or ridged to reduce contact surface area between the introducer sheath and a patient's anatomy. The interior surface of the sheath wall may be wavy or ridged to reduce contact surface area between the sheath wall and a dilator and/or delivery system that advances therethrough. The exterior surface of the sheath wall may be textured to aid in hydro-coat retention and/or to reduce surface contact area with a patient's anatomy, thereby reducing track forces during insertion and delivery. The introducer sheath wall may include a spine.

12 Claims, 7 Drawing Sheets

(58) Field of Classification Search
CPC ............ A61M 25/0023; A61M 25/005; A61M 25/0662; A61M 2025/0024; A61M 2025/0025; A61M 2025/0687
See application file for complete search history.

(56) References Cited

U.S. PATENT DOCUMENTS

| | | | |
|---|---|---|---|
| 2008/0015625 | A1 | 1/2008 | Ventura et al. |
| 2010/0130937 | A1 | 5/2010 | Voss |
| 2010/0198519 | A1 | 8/2010 | Voss et al. |
| 2011/0152763 | A1 | 6/2011 | Bishop et al. |
| 2014/0121629 | A1 | 5/2014 | Macaulay et al. |
| 2016/0213882 | A1 | 7/2016 | Fitterer et al. |
| 2017/0296221 | A1 | 10/2017 | Di Caprio et al. |
| 2019/0008308 | A1 | 1/2019 | Tassoni, Jr. et al. |
| 2020/0330667 | A1 | 10/2020 | Fantuzzi et al. |
| 2022/0233814 | A1 | 7/2022 | Mullins et al. |
| 2023/0029837 | A1 | 2/2023 | Yadav et al. |

OTHER PUBLICATIONS

Communication Pursuant to Article 94(3) EPC, European Patent Application No. 24 171 561.4, mailed Jun. 3, 2026, 7 pages.

* cited by examiner 118
116
115
128
122
110
T3

124
126

114
115
116
118
110
122
112

116
118
200
D5
D4
D7
D6
115
122

115, 118
110

115, 118
110

EXPANDABLE INTRODUCER

CROSS-REFERENCE TO RELATED APPLICATIONS

The present application claims the benefit of U.S. Provisional Application No. 63/498,841, filed Apr. 28, 2023, the contents of which are incorporated by reference herein in their entirety.

FIELD OF THE INVENTION

The present invention relates to an introducer device for providing percutaneous access to a patient's vasculature for a transcatheter device delivery system, and, more particularly to an expandable introducer device having an expandable introducer sheath for accommodating passage of the transcatheter device delivery system therethrough.

BACKGROUND

An introducer device is used to provide percutaneous access to the vascular system of a patient and functions to permit the introduction and positioning of various minimally invasive delivery devices within the patient's vasculature. In general, having the smallest insertion profile is the most desirable and leads to less complications, less trauma, and improved patient outcomes. Some delivery devices, however, are large and require large sheaths to accommodate and help deliver them to the desired site within the body.

BRIEF SUMMARY OF THE INVENTION

The present application is directed to introducers. Non-limiting examples of introducers include the following.

In a first example hereof, an expandable introducer comprises an introducer hub and an introducer sheath coupled to the introducer hub and extending distally therefrom. The introducer sheath includes a sheath wall having an interior surface defining a lumen of the introducer sheath and an exterior surface disposed radially outward from the interior surface. A portion of the sheath wall has a varying thickness around a circumference of introducer sheath.

In a second example hereof, in the expandable introducer of any of the previous or subsequent examples hereof, the introducer sheath is radially expandable from a folded, unexpanded state to an unfolded, expanded state, the introducer sheath includes a folded region and a non-folded region when the introducer sheath is in the folded, unexpanded state, and the varying thickness of the sheath wall includes a first thickness at the folded region and a second thickness at the unfolded region, wherein the second thickness is larger than the first thickness.

In a third example hereof, in the expandable introducer of any of the previous or subsequent examples hereof, the exterior surface of the sheath wall is textured to aid in hydro-coat retention or reduce surface contact area with a patient's anatomy, thereby reducing track forces during insertion and delivery.

In a fourth example hereof, in the expandable introducer of any of the previous or subsequent examples hereof, the sheath wall includes a spine at the non-folded region of the introducer sheath.

In a fifth example hereof, in the expandable introducer of any of the previous or subsequent examples hereof, the exterior surface of the sheath wall is wavy or ridged.

In a sixth example hereof, in the expandable introducer of any of the previous or subsequent examples hereof, an inner diameter of the introducer sheath remains constant along a length of the introducer sheath and a thickness of the sheath wall varies longitudinally such that the exterior surface is wavy or ridged.

In a seventh example hereof, in the expandable introducer of any of the previous or subsequent examples hereof, the exterior surface and the interior surface of the sheath wall are wavy or ridged.

In an eighth example hereof, in the expandable introducer of any of the previous or subsequent examples hereof, a thickness of the sheath wall is constant longitudinally, and wherein an inner diameter and an outer diameter of the introducer sheath varies longitudinally such that the exterior surface and the interior surface are wavy or ridged.

In a ninth example hereof, in the expandable introducer of any of the previous or subsequent examples hereof, the interior surface of the sheath wall is circumferentially ridged.

In a tenth example hereof, in the expandable introducer of any of the previous or subsequent examples hereof, a thickness of the sheath wall varies circumferentially such that the interior surface of the sheath wall is circumferentially ridged.

In an eleventh example hereof, an expandable introducer comprises an introducer hub, and an introducer sheath coupled to the introducer hub and extending distally therefrom. The introducer sheath includes a sheath wall having an interior surface defining a lumen of the introducer sheath and an exterior surface disposed radially outward from the interior surface, and a spine coupled to the sheath wall and extending longitudinally along the sheath wall.

In a twelfth example hereof, in the expandable introducer of any of the previous or subsequent examples hereof, the exterior surface of the sheath wall is textured to aid in hydro-coat retention or reduce surface contact area with a patient's anatomy, thereby reducing track forces during insertion and delivery.

In a thirteenth example hereof, in the expandable introducer of any of the previous or subsequent examples hereof, a portion of the sheath wall has a varying thickness around a circumference of introducer sheath.

In a fourteenth example hereof, in the expandable introducer of any of the previous or subsequent examples hereof, the introducer sheath is radially expandable from a folded, unexpanded state to an unfolded, expanded state, the introducer sheath includes a folded region and a non-folded region when the introducer sheath is in the folded, unexpanded state, and the varying thickness of the sheath wall includes a first thickness at the folded region and a second thickness at the unfolded region, wherein the second thickness is larger than the first thickness.

In a fifteenth example hereof, in the expandable introducer of any of the previous or subsequent examples hereof, the exterior surface of the sheath wall is wavy or ridged.

In a sixteenth example hereof, in the expandable introducer of any of the previous or subsequent examples hereof, an inner diameter of the introducer sheath remains constant along a length of the introducer sheath and a thickness of the sheath wall varies longitudinally such that the exterior surface is wavy or ridged.

In a seventeenth example hereof, in the expandable introducer of any of the previous or subsequent examples hereof, the exterior surface and an interior surface of the sheath wall are wavy or ridged.

In an eighteenth example hereof, in the expandable introducer of any of the previous or subsequent examples hereof, a thickness of the sheath wall is constant longitudinally, and wherein an inner diameter and an outer diameter of the introducer sheath varies longitudinal that that the exterior surface and the interior surface are wavy or ridged.

In a nineteenth example hereof, in the expandable introducer of any of the previous or subsequent examples hereof, the interior surface of the sheath wall is circumferentially ridged.

In a twentieth example hereof, in the expandable introducer of any of the previous or subsequent examples hereof, a thickness of the sheath wall varies circumferentially such that the interior surface of the sheath wall is circumferentially ridged.

In a twenty-first example hereof, an expandable introducer comprises an introducer hub and an introducer sheath coupled to the introducer hub and extending distally therefrom. The introducer sheath includes a sheath wall having an interior surface defining a lumen of the introducer sheath and an exterior surface disposed radially outward from the interior surface. The exterior surface of the sheath wall is wavy or ridged.

In a twenty-second example hereof, in the expandable introducer of any of the previous or subsequent examples hereof, an inner diameter of the introducer sheath remains constant along a length of the introducer sheath and a thickness of the sheath wall varies longitudinally such that the exterior surface is wavy or ridged.

In a twenty-third example hereof, in the expandable introducer of any of the previous or subsequent examples hereof, the exterior surface of the sheath wall is textured to aid in hydro-coat retention or reduce surface contact area with a patient's anatomy, thereby reducing track forces during insertion and delivery.

In a twenty-fourth example hereof, in the expandable introducer of any of the previous or subsequent examples hereof, the introducer sheath is radially expandable from a folded, unexpanded state to an unfolded, expanded state, and the introducer sheath includes a folded region and a non-folded region when the introducer sheath is in the folded, unexpanded state.

In a twenty-fifth example hereof, in the expandable introducer of any of the previous or subsequent examples hereof, the introducer sheath includes a spine coupled to the sheath wall and extending longitudinally.

In a twenty-sixth example hereof, in the expandable introducer of any of the previous or subsequent examples hereof, the interior surface of the sheath wall is circumferentially ridged.

In a twenty-seventh example hereof, in the expandable introducer of any of the previous or subsequent examples hereof, a thickness of the sheath wall varies circumferentially such that the interior surface of the sheath wall is circumferentially ridged.

In a twenty-eighth example hereof, an expandable introducer comprises an introducer hub and an introducer sheath coupled to the introducer hub and extending distally therefrom. The introducer sheath includes a sheath wall having an interior surface defining a lumen of the introducer sheath and an exterior surface disposed radially outward from the interior surface. The exterior surface of the sheath wall is wavy or ridged and the interior surface of the sheath wall is wavy or ridged.

In a twenty-ninth example hereof, in the expandable introducer of any of the previous or subsequent examples hereof, a thickness of the sheath wall is constant longitudinally, and an inner diameter and an outer diameter of the introducer sheath varies longitudinal such that the exterior surface and the interior surface are wavy or ridged.

In a thirtieth example hereof, in the expandable introducer of any of the previous or subsequent examples hereof, the exterior surface of the sheath wall is textured to aid in hydro-coat retention or reduce surface contact area with a patient's anatomy, thereby reducing track forces during insertion and delivery.

In a thirty-first example hereof, in the expandable introducer of any of the previous or subsequent examples hereof, the introducer sheath is radially expandable from a folded, unexpanded state to an unfolded, expanded state, the introducer sheath includes a folded region and a non-folded region when the introducer sheath is in the folded, unexpanded state, and a first thickness of the folded region of the sheath wall is less than a second thickness of the non-folded region of the sheath wall.

In a thirty-second example hereof, in the expandable introducer of any of the previous or subsequent examples hereof, the introducer sheath further includes a spine coupled to the sheath wall, the spine extending longitudinally.

In a thirty-third example hereof, in the expandable introducer of any of the previous or subsequent examples hereof, the spine extends along the non-folded region of the introducer sheath.

In a thirty-fourth example hereof, in the expandable introducer of any of the previous or subsequent examples hereof, the interior surface of the sheath wall is circumferentially ridged.

In a thirty-fifth example hereof, in the expandable introducer of any of the previous or subsequent examples hereof, a thickness of the sheath wall varies circumferentially such that the interior surface is circumferentially ridged.

In a thirty-sixth example hereof, an expandable introducer comprises an introducer hub and an introducer sheath coupled to the introducer hub and extending distally therefrom. The introducer sheath includes a sheath wall having an interior surface defining a lumen of the introducer sheath and an exterior surface disposed radially outward from the interior surface. The interior surface of the sheath wall is circumferentially ridged such that inner radius of the introducer sheath varies circumferentially.

In a thirty-seventh example hereof, in the expandable introducer of any of the previous or subsequent examples hereof, an outer radius of the introducer sheath is constant, wherein a thickness of the sheath wall varies such that the inner radius varies circumferentially.

In a thirty-eighth example hereof, in the expandable introducer of any of the previous or subsequent examples hereof, the exterior surface of the sheath wall is textured to aid in hydro-coat retention or reduce surface contact area with a patient's anatomy, thereby reducing track forces during insertion and delivery.

In a thirty-ninth example hereof, in the expandable introducer of any of the previous or subsequent examples hereof, the introducer sheath is radially expandable from a folded, unexpanded state to an unfolded, expanded state.

In a fortieth example hereof, in the expandable introducer of any of the previous or subsequent examples hereof, the introducer sheath includes a folded region and a non-folded region when the introducer sheath is in the folded, unexpanded state.

In a forty-first example hereof, in the expandable introducer of any of the previous or subsequent examples hereof, the introducer sheath further includes a spine disposed coupled to the sheath wall, wherein in the spine extends longitudinally.

In a forty-second example hereof, in the expandable introducer of any of the previous or subsequent examples hereof, the spine is coupled to the non-folded region of the introducer sheath.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings may not be to scale.

DETAILED DESCRIPTION

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a delivery system. The following detailed description is merely exemplary in nature and is not intended to limit the invention of the application and uses of the invention. Furthermore, there is no intention to be bound by any expressed or implied theory presented in the preceding field of the invention, background, summary or the following detailed description.

As used in this specification, the singular forms “a”, “an” and “the” specifically also encompass the plural forms of the terms to which they refer, unless the content clearly dictates otherwise. The term “about” is used herein to mean approximately, in the region of, roughly, or around. When the term “about” is used in conjunction with a numerical range, it modifies that range by extending the boundaries above and below the numerical values set forth. In general, the term “about” is used herein to modify a numerical value above and below the stated value by a variance of 5%. It should be understood that use of the term “about” also includes the specifically recited number of value.

The terms “proximal” and “distal” herein when used with respect to a delivery system are used with reference to the clinician using the devices. Therefore, “proximal” and “proximally” mean in the direction toward the clinician, and “distal” and “distally” mean in the direction away from the clinician.

As used herein, the term “generally” and “substantially” mean approximately. When used to describe angles such as “substantially parallel” or “substantially perpendicular” the term “substantially” means within 10 degrees of the angle. When used to describe shapes such as “substantially” or “generally” cylindrical or “substantially” or “generally” tube-shaped or “generally” or “substantially” conical, the terms mean that the shape would appear cylindrical or tube-shaped or conical to a person of ordinary skill in the art viewing the shape with a naked eye.

Figure 1:
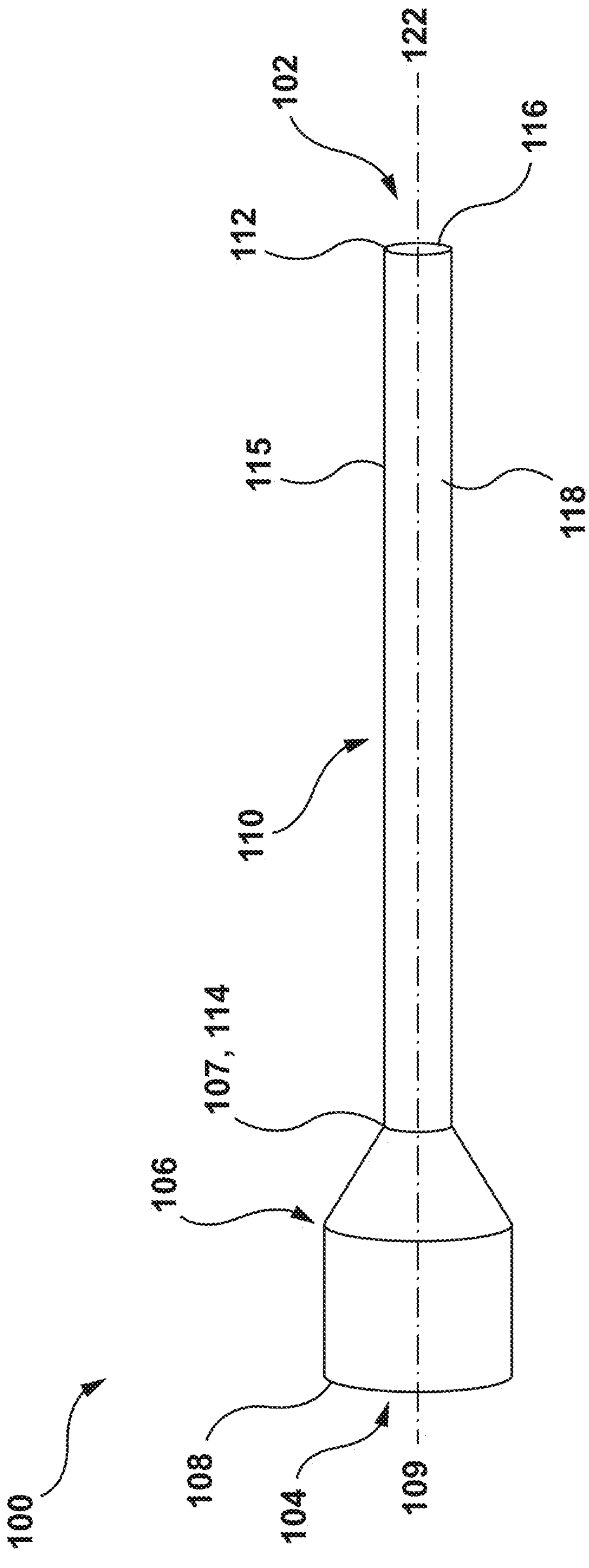
FIG. 1 depicts a side view of an expandable introducer according to embodiments hereof.

FIG. 1 shows an expandable introducer 100 according to embodiments hereof. The expandable introducer 100 includes an introducer hub 106 and an introducer sheath 110. The expandable introducer 100 includes a distal end 102 and a proximal end 104. The introducer sheath 110 is coupled to a distal end 107 of the introducer hub 106 and extends distally therefrom.

The introducer hub 106 includes the distal end 107, a proximal end 108, and a passageway 109 extending from the proximal end 108 to the distal end 107 of the introducer hub 106. The passageway 109 is sized and shaped to accommodate a delivery system therethrough, as described in more detail below. An exterior surface of the introducer hub 106 tapers in a distal direction, as shown in FIG. 1. The introducer hub 106 may further include a seal (not shown) disposed within the passageway 109 to seal around a dilator shaft of a dilator (not shown) or the delivery system, and prevent blood flow out of a patient’s vessel when the introducer 100 is in use.

The introducer sheath 110 is a substantially flexible, plastic tube defining a lumen 122 of the introducer sheath 110. The sheath 110 includes a distal end 112, a proximal end 114, and a sheath wall 115. The sheath wall 115 includes an interior or inner surface 116 defining the lumen 122 and an exterior or outer surface 118, as best shown in FIG. 1. The thickness of the wall 115 of the introducer sheath 110 is defined by the distance between the interior surface 116 and exterior surface 118 of the sheath wall 115. The lumen 122 is sized and shaped to accommodate a dilator or delivery system therethrough, as explained in further detail below. The introducer sheath 110 may have a longitudinal length of about 370 mm and may comprise low friction flexible materials such as, but not limited to, polyvinyl chloride (PVC), polyethylene terephthalate (PET), and/or any other materials known to those skilled in the art.

At least a portion of the introducer sheath 110 is configured to be folded into a folded or unexpanded configuration during insertion within a vessel of a patient and can be unfolded to an unfolded or expanded configuration via advancement of a dilator or delivery system through the lumen 122 of the introducer sheath 110, as shown and explained with reference to FIGS. 2A-2B and 3A-3B below. FIGS. 2A-2B and 3A-3B show cross sections of the introducer sheath 110 according to embodiments herein. When the introducer sheath 110 is in the folded or unexpanded configuration, the introducer sheath 110 includes a folded region 124 and a non-folded region 126, as shown in FIGS. 2A and 3A. The folded region 124 is defined as the region where a section of the introducer sheath 110 is folded over. In other words, a portion of the introducer sheath 110 is folded and bent to overlap with itself. The non-folded region 126 of the introducer sheath 110 is defined as the remainder of the introducer sheath 110 that does not include a fold. As can be seen in FIGS. 2A and 3A, when folded, the introducer sheath 110 includes two folds or bends.

Figure 2B:
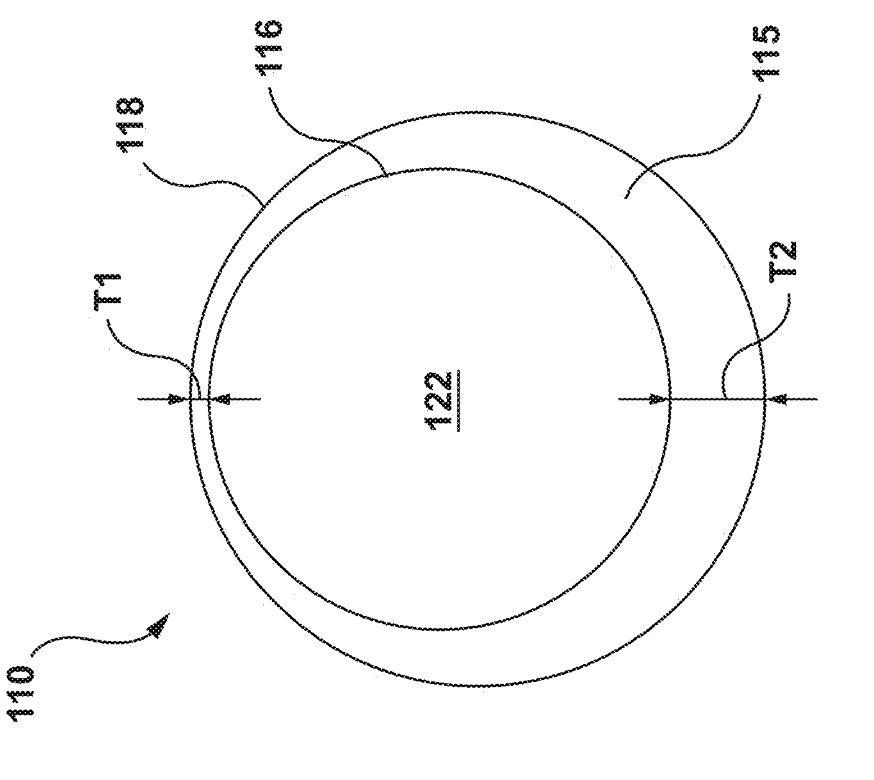
FIG. 2B depicts a cross-section of the introducer sheath of FIG. 2A in an unfolded or expanded configuration according to embodiments hereof.
Figure 2A:
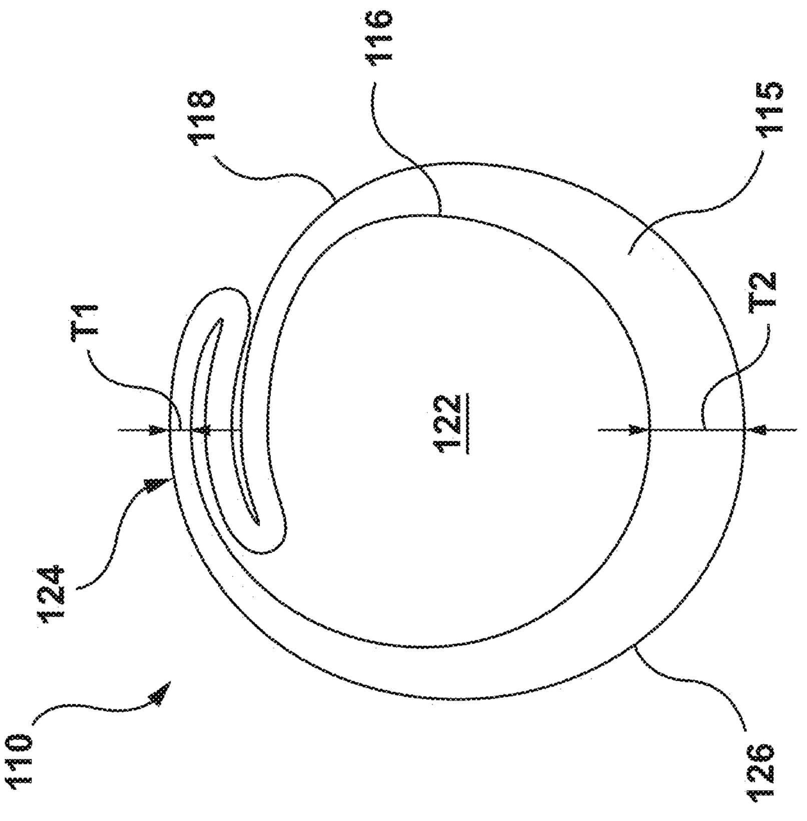
FIG. 2A depicts a cross-section of an introducer sheath in a folded or unexpanded configuration according to embodiments hereof.
Figures 3A, 3B:
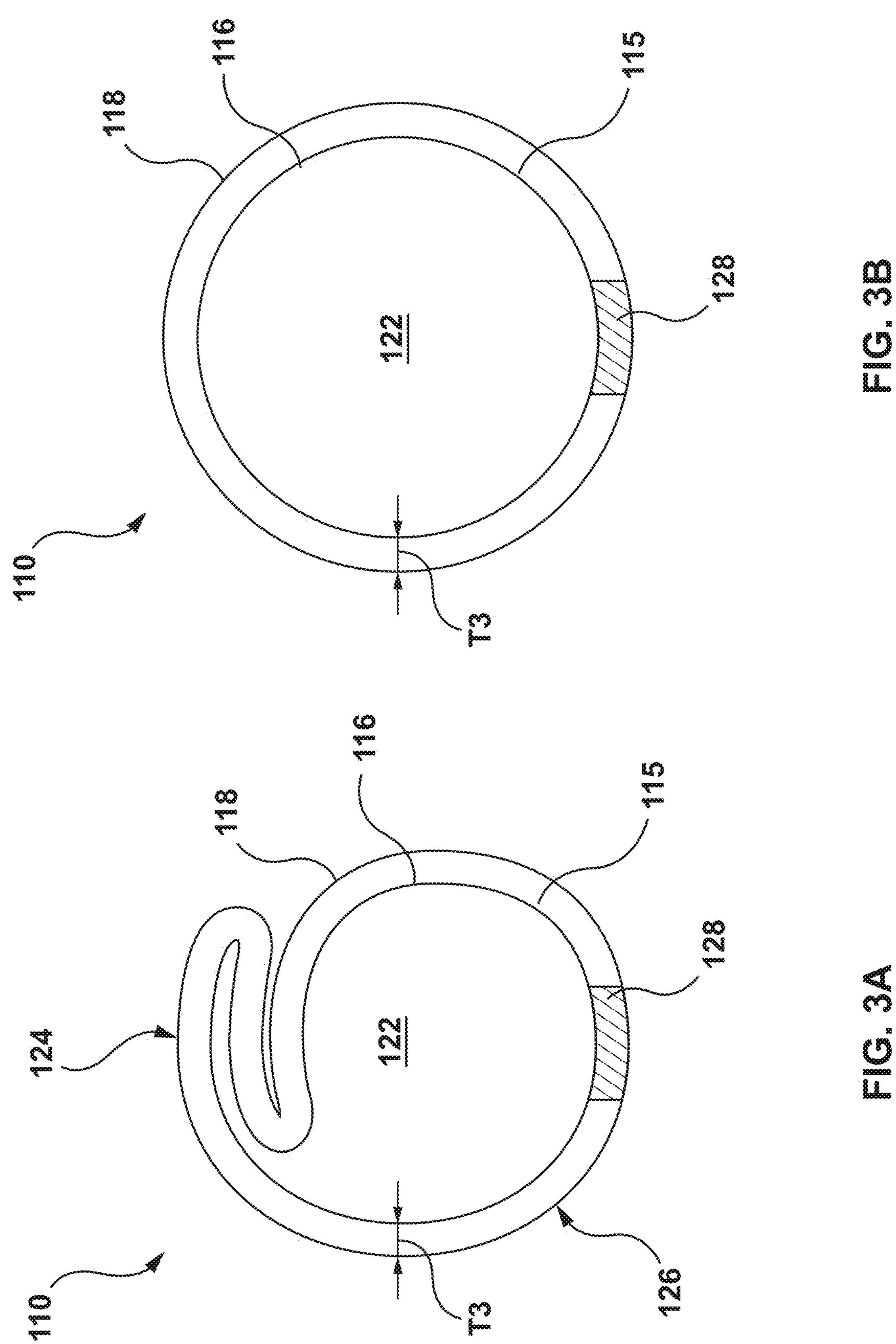
FIG. 3A depicts a cross-section of an introducer sheath in a folded or unexpanded configuration according to embodiments hereof.
FIG. 3B depicts a cross-section of the introducer sheath of FIG. 3A in an unfolded or expanded configuration according to embodiments hereof.

In the embodiment shown in FIGS. 2A-2B, the introducer sheath 110 has a varying thickness around a circumference of the introducer sheath 110. In particular, the wall 115 of the introducer sheath 110 has a first thickness T1 and second thickness T2, wherein the second thickness T2 is greater than the first thickness T1. In the embodiment shown, the first thickness T1 is in the portion of the wall circumference that becomes the folded portion 124 when the introducer sheath 110 is in the folded configuration, as shown in FIG. 2A. As can be seen, in FIG. 2B, the varying wall thickness is also present in the unfolded or expanded configuration. Although the wall 115 has been described as having a first wall thickness T1 and a second wall thickness T2, the thickness may vary such that the wall thickness varies between the first wall thickness T1 and the second wall thickness T2. In other words, as shown in FIGS. 2A and 2B, the wall thickness varies from the first wall thickness T1 to the second wall thickness T2. For example, the wall thickness was increase continuously from the first wall thickness T1 to the second wall T2, and/or may have steps to change the thicknesses between the first wall thickness T1 and the second wall thickness T2. The first thickness T1 of the folded region 124 of the introducer sheath 110 can range from about 0.05 mm to about 0.15 mm and the second thickness T2 of the non-folded region 126 of the introducer sheath 110 can range from about 0.4 mm to about 0.7 mm. The increased thickness (T2) of the non-folded region 126 of the introducer sheath 110 prevents kinking and provides support to the introducer sheath 110 by providing column strength to the introducer sheath 110.

As explained above, advancement of a dilator or delivery system through the lumen 122 of the introducer sheath 110 causes the introducer sheath 110 to unfold or expand to the expanded configuration. FIG. 2B shows the introducer sheath 110 in the expanded or unfolded configuration. As the dilator or delivery system is advanced through the lumen 122, the folded region 124 of the introducer sheath 110 unfolds such that a diameter of the lumen 122 introducer sheath 110 increases to accommodate passage of the dilator or delivery system through the lumen 122 of the introducer sheath 110, as shown in FIG. 2B.

In another embodiment, as shown in FIGS. 3A-3B, the sheath wall 115 of the introducer sheath 110 has a constant or fixed thickness T3 around the circumference of the introducer sheath 110. However, in the embodiment of FIGS. 3A-3B, the introducer sheath further includes a spine 128 coupled to or fused within the non-folded portion 126 of the introducer sheath 110. In the embodiment shown, when the introducer sheath 110 is in the folded configuration, the spine 128 is disposed directly across from (i.e., 180 degrees around the circumference) the folded region 124 of the introducer sheath 110, as shown in FIG. 3A. The spine 128 may be fused to the exterior surface 118 of the sheath wall 115, fused to the interior surface 116 of the sheath wall 115, or embedded in between the interior and exterior surfaces 116, 118 of the sheath wall 115, respectively. The spine 128 may be a rigid (i.e., high durometer) polymer material, such as, but not limited to, 72D polyether block amide (PEBAX), a polyamide 12 material (such as VESTAMID), pellethanes, urethanes, or other materials with similar characteristics known to those skilled in the art, or combinations thereof. The spine 128 may provide column strength to the introducer sheath 110. The spine 128 may extend in a substantially straight line longitudinally from the proximal end 114 to the distal end 112 of the introducer sheath 110. However, this is not meant to be limiting, as the spine 128 may be any shape or configuration known to those skilled in the art. For example, in alternate embodiments, the spine 128 may only extend along a portion of the introducer sheath 110. FIG. 3B shows the introducer sheath 110 of FIG. 3A in the expanded configuration. Advancement of a dilator or delivery system through the lumen 122 of the introducer sheath 110 causes the introducer sheath 110 to unfold or expand to the expanded configuration. As the dilator or delivery system is advanced through the lumen 122, the folded region 124 of the introducer sheath 110 unfolds such that an inner diameter of the introducer sheath 110 may increase to accommodate passage of the dilator or delivery system through the lumen 122 of the introducer sheath 110, as shown in FIG. 3B.

Figures 4A, 4B:
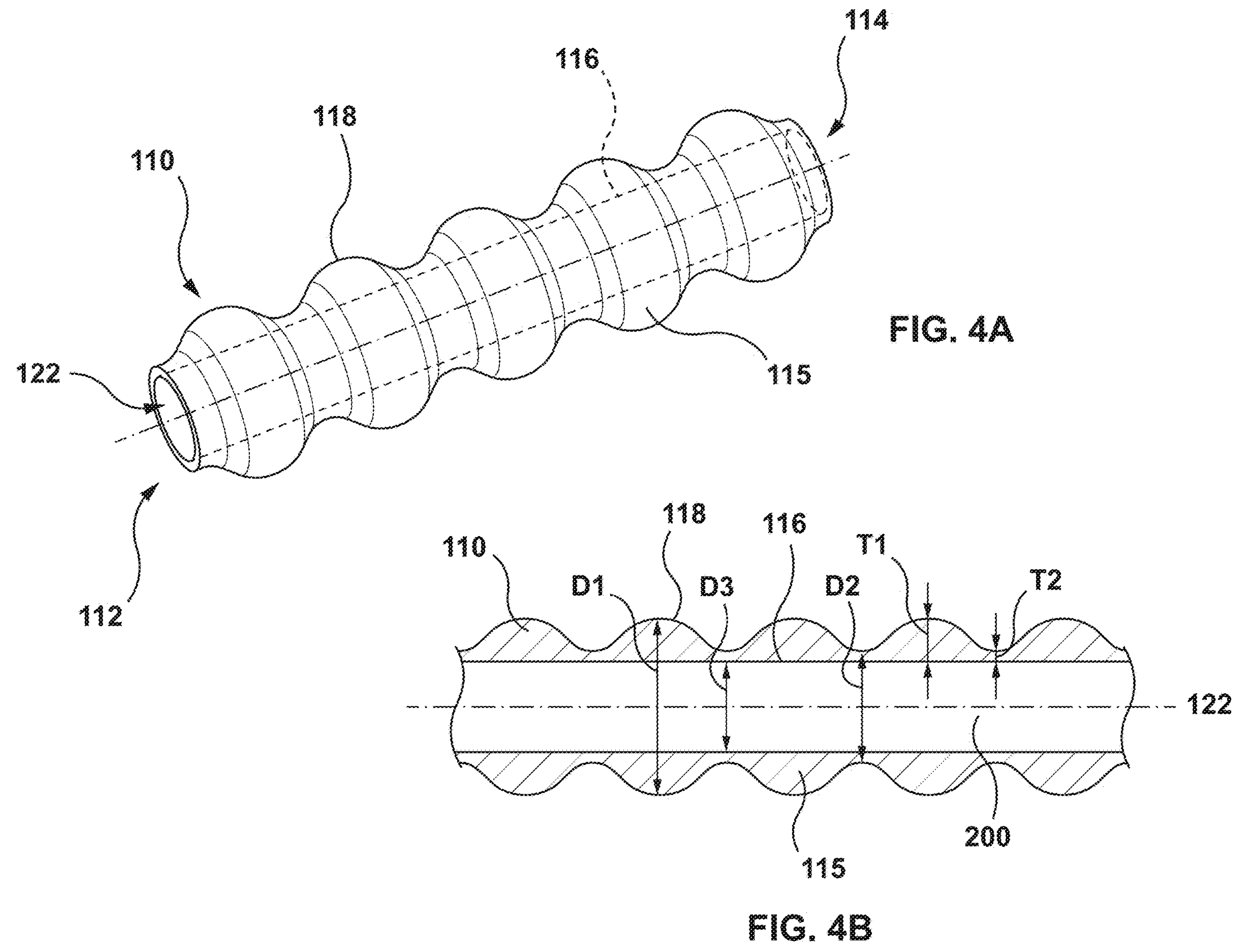
FIG. 4A depicts a perspective side view of an introducer sheath in an unfolded or expanded configuration according to embodiments hereof.
FIG. 4B depicts a side view of the introducer sheath of FIG. 4A according to embodiments hereof.

In another embodiment, which may be in combination with the embodiments shown and described with respect to FIGS. 2A-2B and 3A-3B, the sheath wall 115 of the introducer sheath 110 may have a thickness that varies along the longitudinal length of the introducer sheath 110, as shown and described with respect to FIGS. 4A-4B. As shown in the perspective view of the introducer sheath 110 in FIG. 4A, the sheath wall 115 of the introducer sheath 110 includes a ridged or waved exterior surface 118 and the interior surface 116 includes a fixed or constant inner diameter. In other words, the thickness of the sheath wall 115 varies along the longitudinal length of the introducer sheath 110. An inner diameter D3 of the introducer sheath 110, defined by the interior surface 116 of the sheath wall 115, is constant, as shown in FIG. 4B. An outer diameter of the introducer sheath 110, defined by the exterior surface 118 of the sheath wall 115, increases and decreases along the longitudinal length of the introducer sheath 110 in a wave-like configuration between a first outer diameter D1 and a second outer diameter D2, as best shown in FIG. 4B. Due to the inner diameter D3 being constant, the outer diameter varies by varying the thickness of the sheath wall 115 along the longitudinal length of the introducer sheath 110, i.e., varying the distance between the interior surface 116 and the exterior surface 118 of the sheath wall 115, as shown in the longitudinal cross-section of the introducer sheath 110 in FIG. 4B. Thus, the thickness of the sheath wall varies between a first thickness T1 at the first outer diameter D1 and a second thickness T2 at the second outer diameter D2, as shown in FIG. 4B. As can be seen in FIG. 4B, the thickness of the wall 115 varies smoothly between the first thickness T1 and the second thickness T2. Further, the variation occurs a plurality of times to create the wavy exterior surface 118. Still further, although shown in cross-section, it would be understood that the wall thickness at a particular longitudinal location extends around the circumference of the introducer sheath 110. The wavy or ridged exterior surface 118 of the sheath wall 115 reduces track force, as it reduces the amount of contact surface or contact area the introducer sheath 110 has with the native anatomy. In other words, the native anatomy only contacts the introducer sheath wall 115 at the thicker wall portions. The native anatomy does not contact the outer surface 118 of the sheath wall 115 at the smaller thickness portions. This configuration may reduce the need for a coating, as the ridged outer surface 118 reduces the coefficient of friction, compared to an introducer sheath that includes a constant diameter around the exterior surface of the introducer sheath. The thickness of the wall 115 of the introducer sheath 110 can vary from the first thickness T1 of about 0.005 inch to about 0.015 inch and the second thickness T2 of about 0.01 inch to about 0.045 inch. In embodiments, the second thickness T2 can be from about 50% greater to about 300% greater, or about 100% greater to about 200% greater, than the first thickness T1. As can be seen, the lumen 122 of the introducer sheath 110, defined by the interior surface 116 of the sheath wall 115, and is sized and shaped to accommodate passage of a dilator or delivery system 200 therethrough.

Figures 5A, 5B:
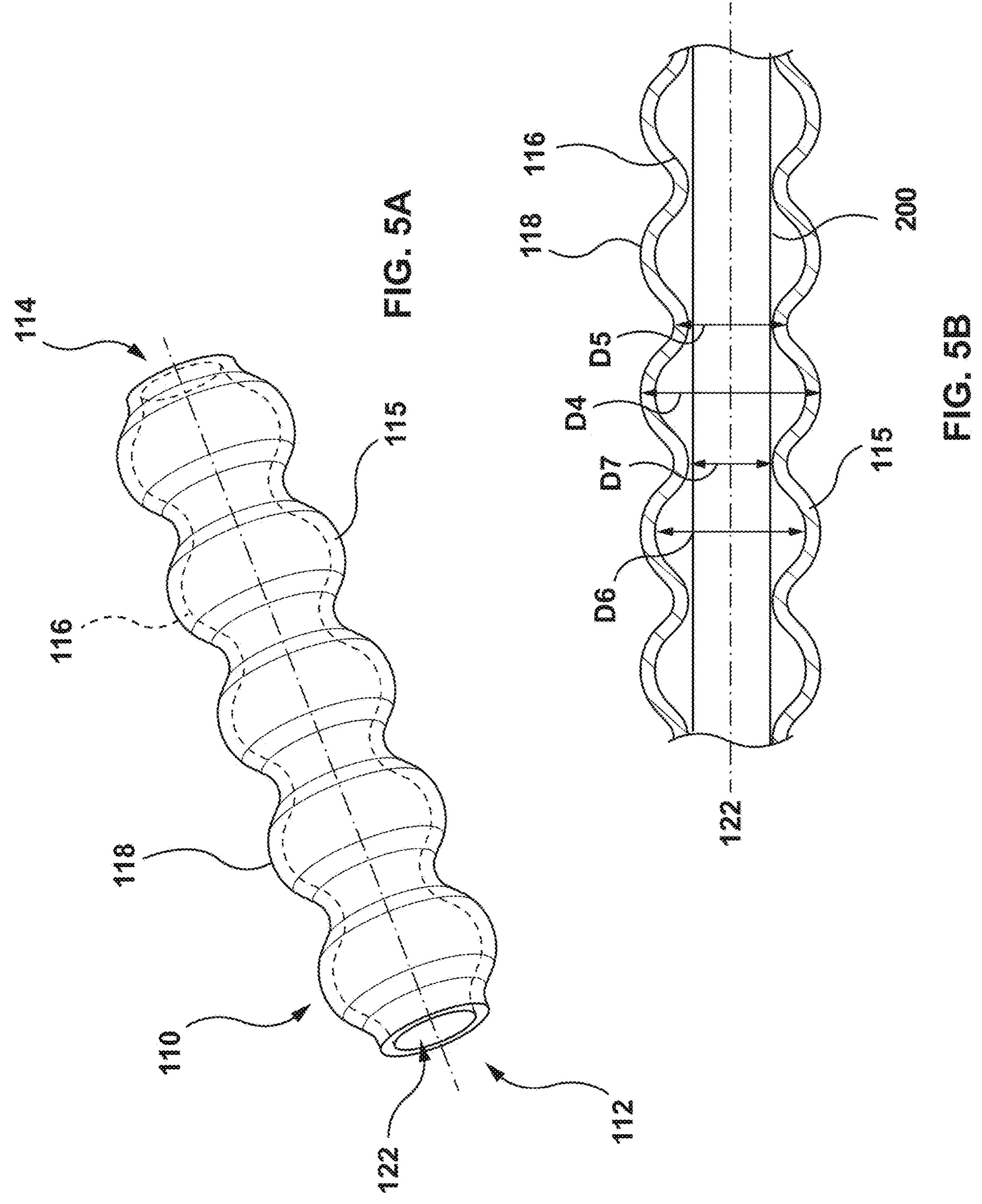
FIG. 5A depicts a perspective side view of an introducer sheath in an unfolded or expanded configuration according to embodiments hereof.
FIG. 5B depicts a side view of the introducer sheath of FIG. 5A according to embodiments hereof.

In another embodiment, which may be in combination with embodiments shown and described with respect to FIGS. 2A-2B and 3A-3B, the introducer sheath 110 includes a ridged or wavy exterior surface 118 and a ridged or wavy interior surface 116, as shown in FIGS. 5A and 5B. In this embodiment, because both the interior surface 116 and the exterior surface 118 are wavy, the thickness of the sheath wall 115 may be constant, as shown in FIG. 5B. As further shown in FIG. 5B, the introducer sheath 110 includes a first outer diameter D4 and a second outer diameter D5 that is smaller than the first outer diameter D4. Further, the outer diameter of the introducer sheath 110 continuously decreases from the first outer diameter D4 to the second outer diameter D5. The outer diameter of the introducer sheath 110 repeats a pattern of reducing and increasing to form the wavy outer surface of the sheath wall 115. Similarly, the introducer sheath 110 includes a first inner diameter D6 and a second inner diameter D7 that is smaller than the first inner diameter D6. Further, the inner diameter of the introducer sheath 110 continuously decreases from the first inner diameter D6 to the second inner diameter D7. The inner diameter of the introducer sheath 110 repeats a pattern of reducing and increasing to form the wavy interior surface 116 of the introducer sheath 110. The waves of the inner and outer surfaces 116, 118 match or mirror each other such that the first (larger) outer diameter D4 and the first (larger) inner diameter D6 are aligned, and the second (smaller) outer diameter D5 and the second (smaller) inner diameter D7 are aligned.

The ridged exterior surface 118 of the sheath wall 115 reduces track force, as it reduces the amount of contact surface the introducer sheath 110 has with the anatomy. This reduces the need for a coating, as the ridged exterior surface 118 reduces the coefficient of friction, compared to an introducer sheath that includes a constant outer diameter around the outer surface of the introducer sheath. The ridged or waved interior surface 116 of the sheath wall 115 reduces surface contact area between the interior surface 116 of the sheath wall 115 and the dilator and/or delivery system that advances through the lumen 122 of the introducer sheath 110. This, in turn, results in reduced insertion forces when advancing the dilator or delivery system therethrough. In the embodiment shown, the wavy interior surface 116 of the sheath wall 115 extends along the entire longitudinal length of the introducer sheath 110, i.e. from the proximal end 114 to the distal end 112 of the introducer sheath 110. However, this is not meant to be limiting, as the wavy interior surface 116 of the sheath wall 115 may be present only along a portion of the introducer sheath 110, such as, for example, only the distal end 112, or only proximal end 114, or only sections of the introducer sheath 110 that have high insertion forces. Similarly, in the embodiment shown, the wavy exterior surface 118 extends along the entire longitudinal length of the introducer sheath 110, i.e. from the proximal end 114 to the distal end 112 of the introducer sheath 110. However, this is not meant to be limiting, as the wavy exterior surface 118 may be present only along a portion of the introducer sheath 110, such as, for example, only the distal end 112, or only proximal end 114, or only sections of the introducer sheath 110 that have high tracking forces. In an embodiment, the thickness of the introducer sheath wall 115 may be about 0.005 inch to about 0.015 inch. As can be seen, the lumen 122 of the introducer sheath 110, defined by the interior surface 116 of the sheath wall 115, is sized and shaped to accommodate passage of a dilator or a delivery system 200 therethrough.

Figures 7A, 7B:
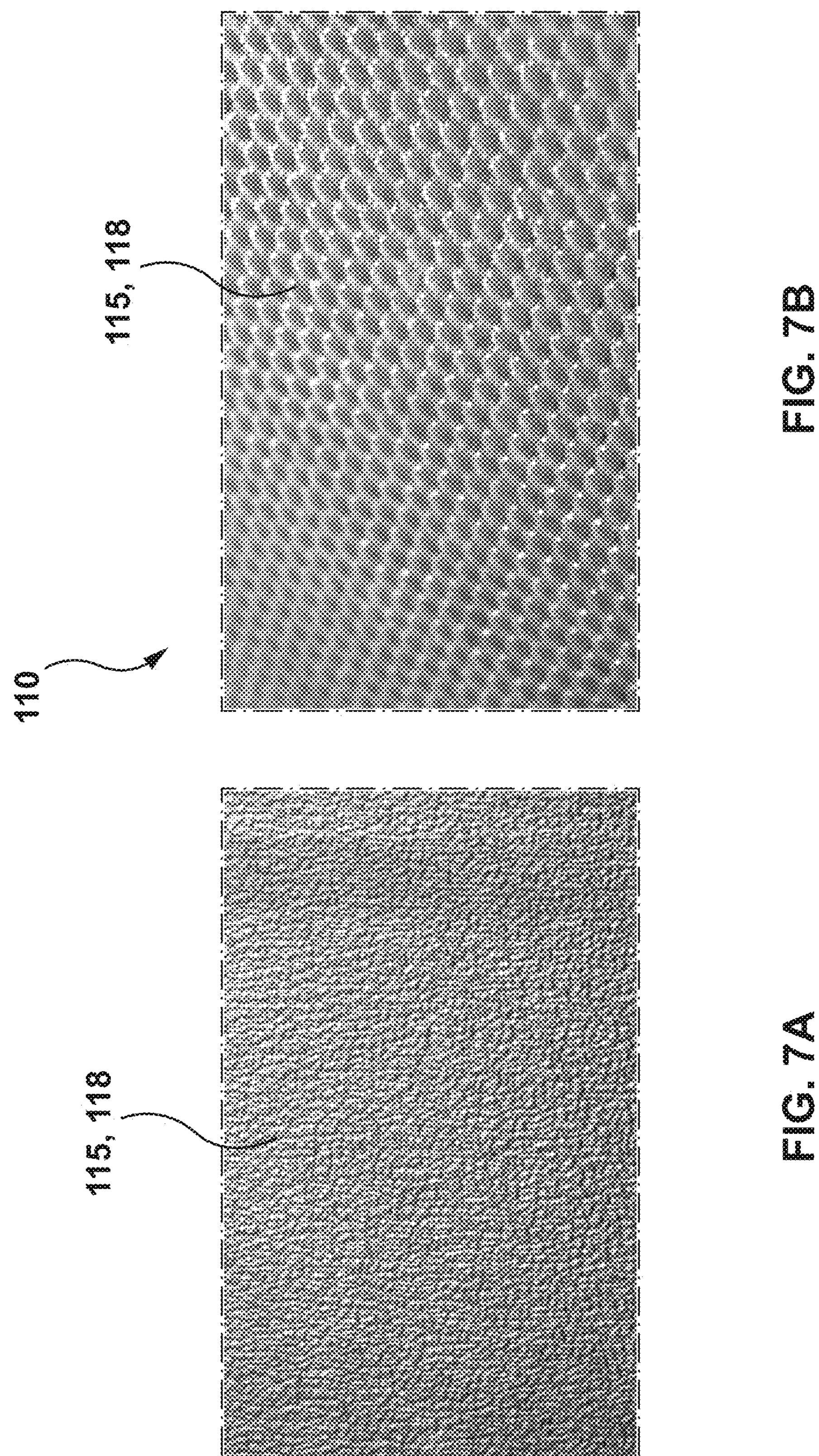
FIGS. 7A-7B depict close-up views of exterior surfaces of an introducer sheath according to embodiments hereof.

In any of the embodiments disclosed herein, the exterior surface 118 of the introducer sheath wall 115 may be textured, as shown in FIGS. 7A and 7B. In other words, the exterior surface 118 of the sheath wall 115 of the introducer sheath 110 may include small ridges, bumps, or depressions that form a texture on the exterior surface 118. The textured exterior surface 118 may be formed by adding ridges, bumps, or depressions to the exterior surface 118 of the material of the wall 115, or the material of the sheath wall 115 may have a texture exterior surface. The textured materials of the outer surface 118 of the sheath wall 115, as shown in FIGS. 7A-7B, include a plurality of small ridges and depressions that aid in hydrocoat retention and reduces the coefficient of friction. The ridges and depressions of the textured materials also reduce the surface contact area with the native anatomy which, in turn, reduces track forces during insertion and delivery when the introducer 100 is in use.

Figures 6A, 6B:
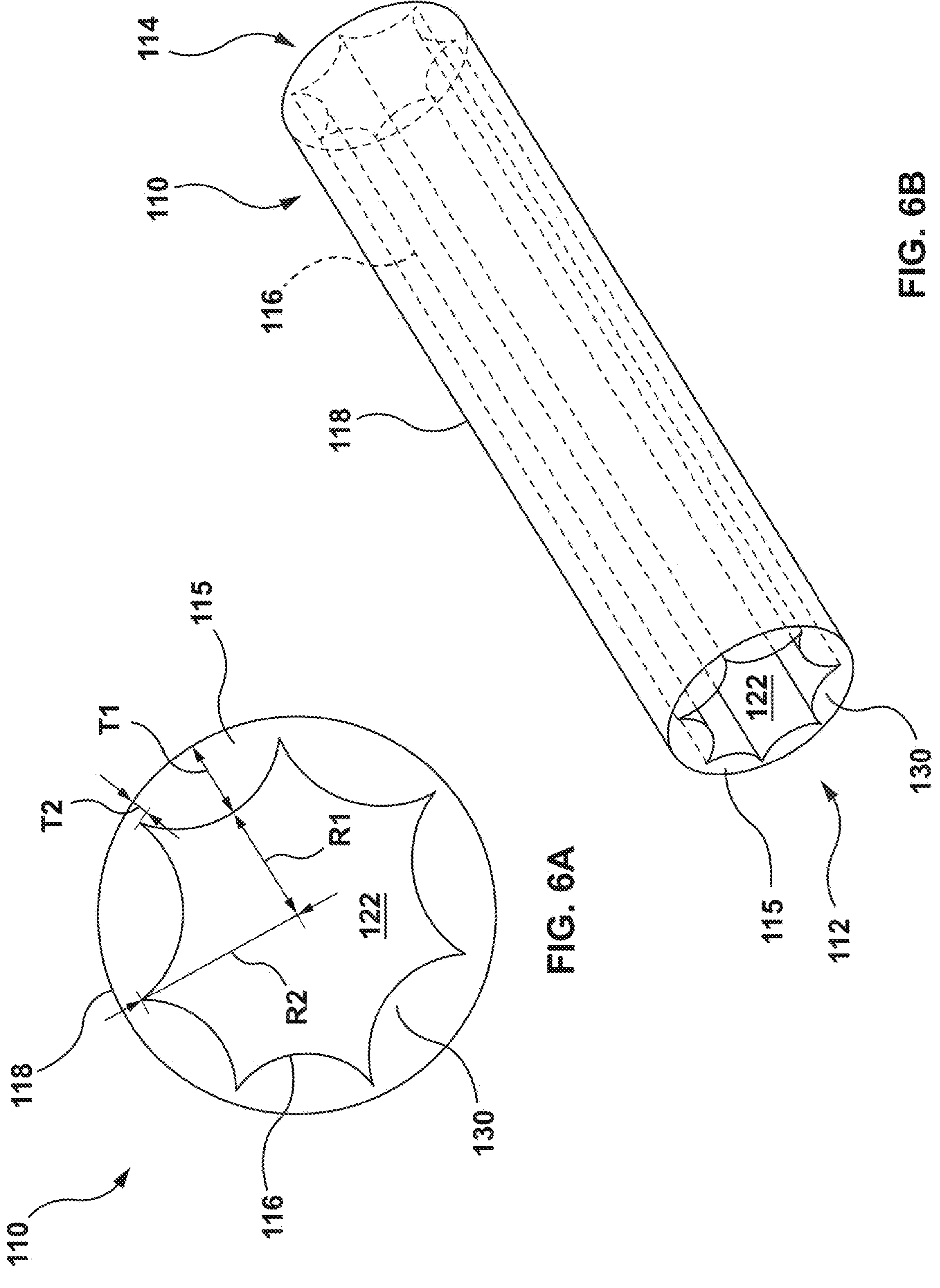
FIG. 6A depicts a cross-section of an introducer sheath in an unfolded or expanded configuration according to embodiments hereof.
FIG. 6B depicts a perspective side view of the introducer sheath of FIG. 6A according to embodiments hereof.

In another embodiment, which may be combined with any of the embodiments described herein, the introducer sheath 110 includes a circumferentially ridged or ribbed interior surface 116, as shown in FIGS. 6A and 6B. FIG. 6A shows a cross-section of an introducer sheath 110 wherein the interior surface 116 of the sheath wall 115 is circumferentially ridged. In other words, the inner diameter of the introducer sheath 110 varies in the circumferential direction, as described in more detail below. This could also be described as creating longitudinal ridges as the larger diameter portions shown in cross-section in FIG. 6A are aligned and the smaller diameter portions shown in cross-section in FIG. 6A are aligned. Referring to FIG. 6A, the sheath wall 115 includes portions with a first thickness T1 and portions with a second thickness T2 smaller than the first thickness T1 around the circumference of the interior surface 116 of the introducer sheath 110. The radius from the center of the lumen 122 to the exterior surface 118 in this embodiment remains constant. Therefore, the variation in the thickness of the wall 115 takes effect on the interior surface 116. Thus, the interior surface 116 varies between a first radius R1 at the first thickness T1 and a second radius R2 at the second thickness T2, wherein the first radius R1 is smaller than the second radius R2. The thicknesses and radii vary around the circumference of the introducer sheath 110 such that there are several thicker portions and several thinner portions. Further, the thickness varies smoothly between the first thicknesses T1 and the second thicknesses T2, as shown. The thicker wall sections may also be referred to as protrusions 130 extending into the lumen 122 of the introducer sheath 110. The protrusions 130 in the embodiment shown are substantially semi-circular shaped in cross-section. The protrusions 130 of the interior surface 116 reduce the contact area or surface area that contacts the dilator and/or delivery system that advances through the lumen 122 of the introducer sheath 110. The reduction in contact area between the introducer sheath 110 and the dilator and/or delivery system reduces the insertion forces needed to advance the dilator and/or delivery system through the lumen 122 of the introducer sheath 110. FIG. 6B shows the protrusions 130 of the interior surface 116 of the sheath wall 115 extending an entire longitudinal length of the introducer sheath 110, i.e. from the proximal end 114 to the distal end 112 of the introducer sheath 110. However, this is not meant to be limiting, as the protrusions 130 extending radially inward from the interior surface 116 of the sheath wall 115 extend only a portion of the introducer sheath 110, such as the distal end 112 portion of the introducer sheath 110, or the proximal end 114 portion, or sections of the introducer sheath 110 that have high insertion forces.

In another embodiment, which may be combined with any of the embodiments described above, the exterior surface 118 of the introducer sheath wall 115 is textured, examples of which are shown in FIGS. 7A and 7B. In some embodiments, a hydro-coat material may be added to the exterior surface 118 of the introducer sheath 110. In such embodiments, a textured exterior surface 118 of the introducer sheath 110 aids in hydro-coat retention. In other embodiments, a hydro-coat material need not be added to the exterior surface 118. In such embodiments, the textured exterior surface 118 reduces the surface contact area with the native anatomy, thereby reducing track forces during insertion and delivery when the introducer 100 is in use.

While the devices and methods have been disclosed herein as used for delivery of a heart valve prosthesis, they may be used for delivery of any catheter-based device (e.g., stent graft, stent, balloon, etc.) and may be used in any suitable blood vessel.

As noted above, it should be understood that various embodiments disclosed herein may be combined in different combinations than the combinations specifically presented in the description and accompanying drawings. For example, the embodiments with wavy inner or outer surface may also include the spine 128 of FIGS. 3A and 3B, or the thickened wall section of FIGS. 2A and 2B. Similarly, the textured surfaces of FIGS. 7A and 7B may be used on any of the other embodiments. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components.

What is claimed is:

1. An expandable introducer comprising:

an introducer hub; and an introducer sheath coupled to the introducer hub and extending distally therefrom, the introducer sheath including a sheath wall, the sheath wall having an interior surface defining a lumen of the introducer sheath and an exterior surface disposed radially outward from the interior surface, wherein the introducer sheath is radially expandable from a folded, unexpanded state to an unfolded, expanded state, wherein in a lateral cross-section the introducer sheath includes a folded region and a non-folded region around a circumference of the introducer sheath when the introducer sheath is in the folded, unexpanded state, and wherein in the unfolded, expanded state the folded region unfolds to radially expand the introducer sheath and the exterior surface is wavy in a longitudinal direction such that an outer diameter of the sheath wall alternates smoothly in a longitudinal direction between a first outer diameter and a second outer diameter, the second outer diameter being larger than the first outer diameter.

2. The expandable introducer of claim 1, wherein the exterior surface of the sheath wall is textured to aid in hydro-coat retention or reduce surface contact area with a patient's anatomy, thereby reducing track forces during insertion and delivery.

3. The expandable introducer of claim 1, wherein an inner diameter of the introducer sheath remains constant along a length of the introducer sheath and a thickness of the sheath wall varies longitudinally such that the exterior surface is wavy.

4. The expandable introducer of claim 1, wherein the interior surface of the sheath wall is wavy in a longitudinal direction such that an inner diameter of the introducer sheath defining the lumen alternates smoothly in a longitudinal direction between a first inner diameter and a second inner diameter, the second inner diameter being larger than the first inner diameter.

5. The expandable introducer of claim 4, wherein a thickness of the sheath wall is constant longitudinally such that the first outer diameter aligns with the first inner diameter and the second outer diameter aligns with the second inner diameter.

6. The expandable introducer of claim 1, further comprising a spine coupled to the sheath wall and extending longitudinally along the sheath wall.

7. The expandable introducer of claim 1, wherein the folded region has exactly two folds in the folded, unexpanded state.

8. An expandable introducer comprising:

an introducer hub; and an introducer sheath coupled to the introducer hub and extending distally therefrom, the introducer sheath including a sheath wall, the sheath wall having an interior surface defining a lumen of the introducer sheath and an exterior surface disposed radially outward from the interior surface, wherein the introducer sheath is radially expandable from a folded, unexpanded state to an unfolded, expanded state, wherein the introducer sheath includes a folded region and a non-folded region when the introducer sheath is in the folded, unexpanded state, wherein in the unfolded, expanded state the exterior surface is wavy in a longitudinal direction such that an outer diameter of the sheath wall alternates smoothly in a longitudinal direction between a first outer diameter and a second outer diameter, the second outer diameter being larger than the first outer diameter, and wherein the sheath wall includes a spine at the non-folded region of the introducer sheath.

9. An expandable introducer comprising:

an introducer hub; and an introducer sheath coupled to the introducer hub and extending distally therefrom, the introducer sheath including a sheath wall, the sheath wall having an interior surface defining a lumen of the introducer sheath and an exterior surface disposed radially outward from the interior surface, wherein the exterior surface of the sheath wall is wavy in a longitudinal direction such that an outer diameter of the sheath wall alternates smoothly in a longitudinal direction a plurality of times between a first outer diameter and a second outer diameter, the second outer diameter being larger than the first outer diameter, and wherein an inner diameter of the introducer sheath remains constant along a length of the introducer sheath and a thickness of the sheath wall varies longitudinally such that the exterior surface is wavy.

10. The expandable introducer of claim 9, wherein the exterior surface of the sheath wall is textured to aid in hydro-coat retention or reduce surface contact area with a patient's anatomy, thereby reducing track forces during insertion and delivery.

11. The expandable introducer of claim 9, wherein the introducer sheath is radially expandable from a folded, unexpanded state to an unfolded, expanded state, and wherein the introducer sheath includes a folded region and a non-folded region when the introducer sheath is in the folded, unexpanded state.

12. The expandable introducer of claim 9, wherein the introducer sheath includes a spine coupled to the sheath wall and extending longitudinally.

* * * * *